United States Patent [19]

Shimizu et al.

[11] Patent Number: 5,026,939
[45] Date of Patent: Jun. 25, 1991

[54] METHOD FOR PRODUCING 4-ISOBUTYLSTYRENE

[75] Inventors: Isoo Shimizu; Yasuo Matsumura, both of Yokohama; Yoshihisa Inomata, Kawasaki, all of Japan

[73] Assignee: Nippon Petrochemicals Company, Limited, Tokyo, Japan

[21] Appl. No.: 190,508

[22] Filed: May 5, 1988

[30] Foreign Application Priority Data

May 6, 1987 [JP] Japan ................... 62-110175
May 6, 1987 [JP] Japan ................... 62-110176

[51] Int. Cl.$^5$ ................................ C07C 4/24
[52] U.S. Cl. ....................... 585/439; 585/411
[58] Field of Search .......... 585/410, 411, 439, 436

[56] References Cited

U.S. PATENT DOCUMENTS 3,062,903 11/1962 Odioso et al. ............. 585/439
4,827,065 5/1989 Shimizu et al. ............ 585/439

FOREIGN PATENT DOCUMENTS 225994 1/1958 Australia ................... 585/439
658827 3/1963 Canada ..................... 585/439
4928499 7/1974 Japan ...................... 585/439
162525 5/1964 U.S.S.R. ................... 585/439

OTHER PUBLICATIONS

*The Chemistry of Catalytic Hydrocarbon Conversions*, Herman Pines, Academic Press, 1981, p. 1, "Acid-Catalyzed Reaction".

Primary Examiner—W. J. Shine
Assistant Examiner—Douglas J. McGinty
Attorney, Agent, or Firm—Scully, Scott, Murphy & Presser

[57] ABSTRACT

A method for producing alkylstyrene which is characterized in that 1,2-di(substituted phenyl)ethane is brought into contact with an acid catalyst at 200° C. to 650° C. in the presence of an inert gas to crack it into alkylstyrene and alkylbenzene. The method of the invention has advantages in that the operation of reaction and separation of reaction mixture are quite easy, the lowering of catalytic activity is small, and unreacted starting material can be reused.

16 Claims, No Drawings

METHOD FOR PRODUCING 4-ISOBUTYLSTYRENE

BACKGROUND OF THE INVENTION (1) Field of the Invention

This invention relates to a novel method for producing alkylstyrenes. Furthermore, the invention relates to a method for producing alkylstyrenes by catalytically cracking 1,2-di(substituted phenyl)ethane in the presence of an acid catalyst.

More particularly, for example, 4-isobutylstyrene is prepared by catalytically cracking 1,2-di(4-isobutylphenyl)ethane. This 4-isobutylstyrene can be used for preparing α-(4-isobutylphenyl)propionic acid (tradename: "ibuprofen") which is useful as a medicine for the relief of pain and inflammation.

(2) Description of Prior Art

The alkylstyrene is a material which is useful as a comonomer for improving weather-proofness of synthetic plastics and as an intermediate in the organic chemical industry. In order to produce this useful alkylstyrene, there have been proposed several methods as follows in which 1,1-di(substituted phenyl)ethane is cracked in the presence of an acid catalyst.

Ind. Eng. Chem., Vol. 46, No. 4, 652 (1954)
J. Chem. Eng. Data, Vol. 9, No. 1, 104 (1964)
I. & E. C. Prod. Res. Dev., Vol 3, No. 1, 16 (1964)

In the above references, it is disclosed that methylstyrene and dimethylstyrene are obtained by cracking 1,1-ditolylethane and 1,1-dixylylethane, respectively. Furthermore, ethylstyrene, isopropylstyrene and tert-butylstyrene are also referred to.

There are other references which disclose more particular methods:

In U.S. Pat. No. 2,420,689 is described a method for producing dimethylstyrene by cracking 1,1-dixylylethane in the presence of a kaolin catalyst.

In U.S. Pat. No. 2,422,318 is described a method for cracking asymmetrical 1,1-diarylethane.

In U.S. Pat. No. 2,864,872 is described a method to use silica as a cracking catalyst.

In U.S. Pat. No. 2,954,413 is described a method for cracking 1,1-dixylylethane in the presence of a fluidized catalyst.

In U.S. Pat. No. 3,025,330 is described a method for producing methylstyrene from 1,1-ditolylethane.

In U.S. Pat. Nos. 2,976,333 and 2,976,334 are described methods for improving the catalysts for cracking.

Furthermore, in U.S. Pat. No. 4,694,100, it is described that 1,1-di(4-isobutylphenyl)ethane is catalytically cracked to prepare 4-isobutylstyrene. According to this reference, the 4-isobutylstyrene is then carbonylated to produce ibuprofen.

In the methods for cracking 1,1-di(substituted phenyl)ethane as disclosed in the above references, not all of the 1,1-di(substituted phenyl)ethane is cracked and converted into alkylstyrene and alkylbenzene, and it cannot be avoided that unreacted 1,1-di(substituted phenyl)ethane remains in the reaction mixture as a matter of course. This is apparent from the fact that the purpose conversion rates in the methods proposed in the above references are from 40% to 60%.

In order to produce economically alkylstyrene by cracking 1,1-di(substituted phenyl)ethane, the reuse of the unreacted 1,1-di(substituted phenyl)ethane is inevitable. That is, it is an inevitable condition for industrially economize the cracking reaction that the fraction mainly containing 1,1-di(substituted phenyl)ethane that is separated from a reaction mixture is used again for a cracking step.

The inventors of the present invention have made extensive investigation with regard to the preparation of alkylstyrene by cracking. As a result, it was found out that the cracking of the fraction as it stands which mainly contains unreacted 1,1-di(substituted phenyl)ethane recovered from the cracking processes of said compound, is undesirable, and in order to solve this problem, the present invention has been accomplished.

That is, in the cracking of 1,1-di(substituted phenyl)ethane in the conventional art, substituted ethylene components which are formed by dehydrogenation caused by a cracking catalyst are contained in the unreacted 1,1-di(substituted phenyl)ethane fraction as shown by the following chemical equation. When the cracking of such material of the unreacted 1,1-di(substituted phenyl)ethane fraction containing the substituted ethylene components is carried out, the life of cracking catalyst is affected undesirably. Of course, it is not economical to separate the substituted ethylene components by an industrial separation method such as distillation because the boiling points of the components are close.

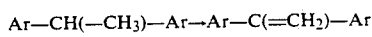

$$Ar—CH(—CH_3)—Ar \rightarrow Ar—C(=CH_2)—Ar$$

wherein Ar is an aryl group.

Accordingly, the method for producing alkylstyrene by cracking 1,1-di(substituted phenyl)ethane is not desirable and the improvement in the method has been sought.

Furthermore, other than the above catalytic cracking, the simple thermal cracking without using any catalyst is not desirable because various components as well as the substituted ethylene components and even polymeric substances are produced together.

BRIEF SUMMARY OF THE INVENTION

It is, therefore, the object of the present invention to provide a novel method for producing alkylstyrene which can be put into practice industrially and economically.

That is, the present invention relates to a method for producing alkylstyrene represented by the following formula (II) which is characterized in that 1,2-di(substituted phenyl)ethane represented by the formula (I) is brought into contact with an acid catalyst at 200° C. to 650° C. in the presence of an inert gas to crack it into alkylstyrene represented by the formula (II) and alkylbenzene represented by the formula (III).

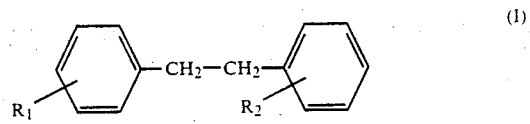

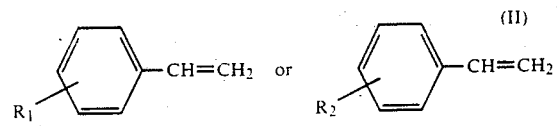

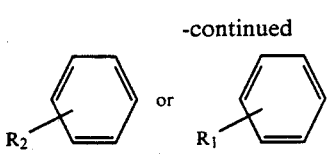

(III)

wherein $R_1$ and $R_2$ are the same or different radicals and each of them is a hydrogen atom or one or more of alkyl groups each having 1 to 4 carbon atoms, and the total number of carbon atoms of the alkyl groups is an integer from 1 to 4.

DETAILED DESCRIPTION OF THE INVENTION

The present invention will be described in more detail.

The 1,2-di(substituted phenyl)ethane used in the present invention has two phenyl groups on the different carbon atoms of ethane and each phenyl group has hydrogen atoms or alkyl groups having 1 to 4 carbon atoms and the total number of the carbon atoms of the alkyl groups is 4 or less. These aryl groups may be either the same ones or different ones. Any of 1,2-di(substituted phenyl)ethane that is prepared by conventionally known method can be used. As a method for producing 1,2-di(substituted phenyl)ethane, there is exemplified a method to react alkylbenzene with 1,2-dichloroethane in the presence of a Friedel-Crafts catalyst such as aluminum chloride.

Among 1,2-di(substituted phenyl)ethanes which can be used in the present invention, exemplified as those of symmetrical compounds are 1,2-diphenylethane, 1,2-ditolylethane, 1,2-dixylylethane, 1,2-di(ethylphenyl)ethane, 1,2-di(trimethylphenyl)ethane, 1,2-di(methylethylphenyl)ethane, 1,2-di(propylphenyl)ethane, 1,2-di(tetramethylphenyl)ethane, 1,2-di(dimethylethylphenyl)ethane, 1,2-di(methylpropylphenyl)ethane, 1,2-di(diethylphenyl)ethane, 1,2-di(n-butylphenyl)ethane, 1,2-di(tert-butylphenyl)ethane, 1,2-di(sec-butylphenyl)ethane and 1,2-di(isobutylphenyl)ethane.

In the method of the present invention, the contact with an acid catalyst is carried out in a diluted condition in the coexistence of an inert gas. As the inert gas, any of methane, ethane and propane as well as inorganic gases such as hydrogen, helium, argon, nitrogen and steam which do not inhibit the acidic activity of the acid catalyst, can be employed. The inert gas can be used either singly or as a mixture of them. In the industrial practice, steam is preferable in view of handling. The rate of dilution with an inert gas or gases is preferably 50 or above when it is represented by [moles of inert gas]/[moles of 1,2-di(substituted phenyl)ethane]. There is no upper limit of the dilution ratio and the larger the better, however, the molar ratio of 500 may be an upper limit in a practical viewpoint.

The acid catalyst to be used are protonic acids, solid acids or protonic acid which is carried on a solid acid. Exemplified as the protonic acids are inorganic protonic acids such as phosphoric acid, sulfuric acid and hydrochloric acid, and heteropoly-acids such as silicotungstic acid and phosphotungstic acid; and organic protonic acids such as benzenesulfonic acid, naphthalenesulfonic acid and toluenesulfonic acid. The solid acids are exemplified by synthetic solid acid catalysts such as silica-alumina, silica-magnesia and amorphous zeolite; natural solid acid catalysts such as activated clay, acid clay, kaolin and attapulgite; and solid catalysts carrying protonic acid such as those in which a protonic acid is impregnated into and carried by an inorganic porous carrier such as silica or alumina having no acidic activity. Among the solid acids, amorphous zeolite is preferable.

The temperature of the contact with the acid catalyst can be properly selected according to the kind of used acid catalyst in the range of 200 to 650° C. More particularly, in the contact with a protonic acid, temperatures in the range of 200 to 350° C. are preferable and, in the contact with a solid acid catalyst, temperatures in the range of 300 to 600° C. are preferable.

In the case of simple thermal cracking without the use of any catalyst, polymeric substances and thermally isomerized substances are produced much which results in the lowering of the yield of alkylstyrene and which cannot be adopted by any possibility in industrial practice.

In the method according to the present invention, the cracking of 1,2-di(substituted phenyl)ethane is carried out in the presence of an acid catalyst under the foregoing conditions of dilution and temperature.

The method for the cracking can be appropriately selected according to the kind of used acid catalyst. When the corrosion of equipment and the convenience for continuous process are taken into consideration, the gas phase contact with a solid acid catalyst or a solid catalyst carrying protonic acid is preferable. The gas phase contact can be carried out under any of atmospheric pressure, raised pressure and reduced pressure as far as 1,2-di(substituted phenyl)ethane is maintained in a gas phase in a diluted condition. The type of reaction may be any of fixed bed, moving bed and fluidized bed.

The catalytic cracking reaction of the present invention is represented by the following chemical formulae:

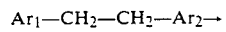

(when it is cracked in the right moiety)

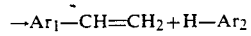

(when it is cracked in the left moiety)

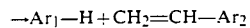

In the above formulae, $Ar_1$ and $Ar_2$ represents the same or different substituted phenyl groups, respectively.

The 1,2-di(substituted phenyl)ethane which is not cracked and remains in the unreacted fraction can be recovered and reused as substantially the same material as the starting 1,2-di(substituted phenyl)ethane.

In the case of symmetrical 1,2-di(substituted phenyl)ethane, that is the substituted phenyl group $Ar_1$ and $Ar_2$ are the same, a single alkylstyrene ($Ar-CH=CH_2$) and a single alkylbenzene (Ar-H) are produced. Accordingly, even though it is possible to use asymmetrical 1,2-di(substituted phenyl)ethane, the use of symmetrical 1,2-di(substituted phenyl)ethane is preferable in practical view point.

The products of the catalytic reaction can be easily separated by conventionally known physical and chemical means. As physical means, for example, separation by solvent extraction utilizing the difference in solubility to a solvent or the difference in distribution coefficients; separation by adsorption utilizing the difference in liability to be adsorbed; separation by crystallization utilizing the difference in melting points or freezing points; and separation by distillation utilizing the difference in boiling points.

Among the above separation means, the separation by distillation is preferable in a practical viewpoint owing to its easiness in operation. The alkylbenzene, alkylstyrene and 1,2-di(substituted phenyl)ethane contained in the reaction mixture in the method of the invention, can be easily separated by the conventional distillation method. In the operation of distillation, it is desirable to carry out under reduced pressure because the thermal polymerization of the aimed product of alkylstyrene is liable to occur.

However, in the case that alkylstyrenes have an alkyl group having 5 or more carbon atoms or they have alkyl groups and the total number of carbon atoms of the alkyl groups is 5 or more, the boiling points of them are high even when the distillation pressure is reduced and the loss by thermal polymerization increases. Therefore, it is not desirable.

The separated fraction mainly containing unreacted 1,2-di(substituted phenyl)ethane can be used intact again for the next cracking process.

When, for instance, 1,2-di(4-isobutylphenyl)ethane is cracked by the method of the present invention, it can be carried out causing neither the transferring nor the isomerization of the isobutyl group nor any side reaction such as decomposition of the isobutyl group. Accordingly, it is possible to produce highly pure 4-isobutylstyrene in a good yield.

The present invention will be described with reference to examples.

EXAMPLE 1

CATALYTIC CRACKING OF 1,2-DIPHENYLETHANE

A silica-alumina catalyst (trademark: N-631-L, made by Nikki Chemical Corp.) of 15 to 25 mesh was prepared. It was fed as deep as 135 mm into a reaction tube of 12 mm in inner diameter made of stainless steel. This was heated to 500° C. by an electric furnace and cracking was carried out by continuously feeding 15 ml/hr of 1,2-diphenylethane and 150 ml/hr of water. After cooling the outlet of the reaction tube, the oily layer was separated from 6 hours to 54 hours after the start of reaction and it was subjected to gas chromatographic analysis.

The results are shown in the following Table 1.

TABLE 1

| Results of Gas Chromatographic Analysis | |
|---|---|
| Fraction | Weight (%) |
| Lighter fraction | 1.7 |
| Benzene fraction | 13.4 |
| Ethylbenzene fraction | 0.5 |
| Styrene fraction | 16.3 |
| Unreacted 1,2-diphenylethane fraction | 67.0 |
| Heavier fraction | 1.1 |

The product of cracking was subjected to precision fractional distillation to obtain a styrene fraction (recovery rate: 87%) in a distillation temperature range of 54 to 58° C. under a reduced pressure of 30 to 35 mmHg and a recovered fraction of unreacted 1,2-diphenylethane (recovery rate: 91%) in a distillation temperature range of 165 to 174° C.

The bromine number of the recovered 1,2-diphenylethane fraction was 0.21. According to mass spectrometry, the content of component of m/e=180 was 0.2% (m/e of 1,1-diphenylethane is 182).

COMPARATIVE EXAMPLE 1

CRACKING OF 1,1-DIPHENYLETHANE

Cracking was carried out in the like manner as in Example 1 using 1,1-diphenylethane as a starting material. After cooling the outlet of the reaction tube, the oily layer was separated from 6 hours to 54 hours after the start of reaction and it was subjected to gas chromatographic analysis. The results are shown in the following Table 2.

TABLE 2

| Results of Gas Chromatographic Analysis | |
|---|---|
| Fraction | Weight (%) |
| Lighter fraction | 1.9 |
| Benzene fraction | 18.8 |
| Ethylbenzene fraction | 1.5 |
| Styrene fraction | 23.0 |
| Unreacted 1,1-diphenylethane fraction | 53.9 |
| Heavier fraction | 0.9 |

The product of cracking was subjected to precision fractional distillation to obtain a styrene fraction (recovery rate: 85%) and a recovered fraction of unreacted 1,1-diphenylethane (recovery rate: 93%) in a distillation temperature range of 148 to 155° C. under a reduced pressure of 30 to 35 mmHg.

The bromine number of the recovered 1,1-diphenylethane fraction was 2.37. According to mass spectrometry, the content of component of m/e=180 was 2.5% (m/e of 1,1-diphenylethane is 182).

EXAMPLE 2

CRACKING OF 1,2-DI(DIMETHYLPHENYL)ETHANE o-Xylene and 1,2-dichloroethane were reacted in the presence of anhydrous AlCl3 catalyst to obtain 1,2-di(dimethylphenyl)ethane (bromine number: 0.1) of 136 to 148° C. in distillation temperature at 3 to 5 mmHg. This was cracked in the like manner as in Example 1.

The cracked product was subjected to precision fractional distillation to obtain a dimethylstyrene fraction (recovery rate: 80%) in a distillation temperature range of 67 to 70° C. under a reduced pressure of 10 to 12 mmHg and a recovered fraction of 1,2-di(dimethylphenyl)ethane (recovery rate: 93%) in a distillation temperature range of 128 to 138° C. under a reduced pressure of 2 to 3 mmHg. The bromine number of the recovered 1,2-di(dimethylphenyl)ethane fraction was 0.2. According to mass spectrometry, the content of component of m/e=236 was 0.3% (m/e of 1,1-di(o-xylyl)ethane is 238).

COMPARATIVE EXAMPLE 2

CRACKING OF 1,1-DI(DIMETHYLPHENYL)ETHANE o-Xylene and acetaldehyde were reacted in the presence of sulfuric acid catalyst to obtain 1,1-di(dimethylphenyl)ethane (bromine number=0.27) of 146 to 151° C. in distillation temperature at 3 to 5 mmHg. This was cracked in the like manner as in Example 1.

The cracked product was subjected to precision fractional distillation to obtain a dimethylstyrene fraction (recovery rate: 78%) and a recovered fraction of 1,1-di(dimethylphenyl)ethane (recovery rate: 91%) in a distillation temperature range of 129 to 137° C. under a reduced pressure of 2 to 3 mmHg. The bromine number of the recovered 1,1-di(dimethylphenyl)ethane fraction was 2.17. According to mass spectrometry, the content of component of m/e=236 was 3.0% (m/e of 1,1-di(-dimethylphenyl)ethane is 238).

EXAMPLE 3

CRACKING OF 1,2-DI(BUTYLPHENYL)ETHANE tert-Butylbenzene and 1,2-dichloroethane were reacted in the presence of anhydrous AlCl$_3$ catalyst to obtain 1,2-di(tert-butylphenyl)ethane (bromine number: 0.2, melting point: 137 to 145° C.) of 169 to 178° C. in distillation temperature at 2 to 3 mmHg. This was cracked in the like manner as in Example 1.

The cracked product was subjected to precision fractional distillation to obtain a tert-butylstyrene fraction (recovery rate: 71%) in a distillation temperature range of 79 to 83° C. under a reduced pressure of 6 to 8 mmHg and a recovered fraction of 1,2-di(tert-butylphenyl)ethane (recovery rate: 93%) in a distillation temperature range of 165 to 180° C. under a reduced pressure of 2 to 3 mmHg. The bromine number of the recovered 1,2-di(tert-butylphenyl)ethane fraction was 0.3. According to mass spectrometry, the content of component of m/e=292 was 0.4% (m/e of 1,1-di(tert-butylphenyl)ethane is 294).

COMPARATIVE EXAMPLE 3

CRACKING OF 1,1-DI(BUTYLPHENYL)ETHANE tert-Butylbenzene and acetaldehyde were reacted in the presence of sulfuric acid catalyst to obtain 1,1-di(-tert-butylphenyl)ethane (bromine number: 0.17, melting point: 96 to 97° C.) of 160 to 166° C. in distillation temperature at 2 to 3 mmHg. This was cracked in the like manner as in Example 1.

The cracked product was subjected to precision fractional distillation to obtain a tert-butylstyrene fraction (recovery rate: 73%) and a fraction of 1,1-di(tert-butylphenyl)ethane (recovery rate: 92%) in a distillation temperature range of 159 to 166° C. under a reduced pressure of 2 to 3 mmHg. The bromine number of the recovered 1,1-di(tert-butylphenyl)ethane fraction was 2.17. According to mass spectrometry, the content of component of m/e=292 was 4.0% (m/e of 1,1-di(tert-butylphenyl)ethane is 294).

EXAMPLE 4

RE-CRACKING OF RECOVERED FRACTION

The diphenylethane fractions recovered in Examples 1 to 3 and Comparative Examples 1 to 3 were cracked intact in the like manner as in Example 1 to compare the changes of cracking catalysts with the passage of time.

The results are shown in the following Table 3.

TABLE 3

| Experiment Number | Changes in Ratios of Cracking with the Passage of Time*1 | | | | Content*2 |
|---|---|---|---|---|---|
| | 12 hr | 24 hr | 48 hr | 72 hr | |
| 4-1 (Example 1) | 0.84 | 0.65 | 0.55 | 0.53 | 0.3 |
| 4-2 (Example 2) | 0.83 | 0.63 | 0.53 | 0.51 | 0.5 |
| 4-3 (Example 3) | 0.78 | 0.56 | 0.54 | 0.53 | 0.5 |
| 4-4 (Comp. Ex. 1) | 0.79 | 0.53 | 0.38 | 0.32 | 7.8 |
| 4-5 (Comp. Ex. 2) | 0.77 | 0.47 | 0.34 | 0.28 | 8.6 |
| 4-6 (Comp. Ex. 3) | 0.71 | 0.40 | 0.23 | 0.22 | 9.1 |

Notes
*1 Values relative to the ratio of cracking as 1.00 at 6 hours after the start of reaction.
*2 The content of substituted ethylene component in a diphenylethane fraction. The content is indicated by the intensity of substituted ethylene component at (m/e)-2 in mass spectrometry provided that the intensity of diphenylethane, of which peak is situated at its m/e position, is 100.

EXAMPLE 5

CRACKING WITH SOLID CATALYSTS

The catalytic cracking of 1,2-diphenylethane was carried out in the like manner as in Example 1 with several catalysts in place of the cracking catalyst N-631-L in Example 1.

The results are shown in the following Table 4.

TABLE 4

| Experiment Number | Catalyst | Ratio of Cracking (%) | Content of Substituted Ethylene Component (wt. %) |
|---|---|---|---|
| | Clay-type solid catalyst | | |
| 5-1 | Kaolin clay | 29 | 0.1 |
| 5-2 | Attapulgus clay (made by Nippon Engelhard, Ltd) | 33 | 0.3 |
| | Synthetic silica-alumina solid catalyst | | |
| 5-3 | FCC-HA (trademark, made by Catalyst & Chem. Ind. Co.) | 34 | 0.3 |
| | Zeolite-type solid catalyst | | |
| 5-4 | MR-Z (trademark, made by Catalyst & Chem. Ind. Co.) | 27 | 0.3 |

COMPARATIVE EXAMPLE 4

With the attapulgus clay used in Example 5, 1,1-diphenylethane was cracked in the like manner as in Example 1. The ratio of cracking was 43% and the content of substituted ethylene component in the unreacted 1,1-diphenylethane fraction was 3.9%.

EXAMPLE 6

To a 500 ml reaction vessel equipped with a condenser, stirrer and gas introducing device were fed 148 g of 1,2-di(dimethylphenyl)ethane and 50 g of silicotungstic acid as a catalyst and cracking was carried out by heating to 280° C. When the temperature exceeded 200° C., 1 liter/min of hydrogen gas was supplied from the gas introducing device and it was led to the condenser together with the cracked products to be cooled, thereby collecting the cracked product. The cracking was continued until the generation of cracked product ceased.

The results of gas chromatographic analysis with regard to the distillates are shown in the following Table 5.

TABLE 5

| Results of Gas Chromatographic Analysis | |
|---|---|
| Fraction | Weight (%) |
| Lighter fraction | 2.3 |

TABLE 5-continued

| Results of Gas Chromatographic Analysis | |
|---|---|
| Fraction | Weight (%) |
| Xylene fraction | 37.7 |
| Ethyldimethylbenzene fraction | 3.3 |
| Dimethylstyrene fraction | 28.6 |
| Unreacted fraction | 24.7 |
| Heavier fraction | 3.4 |

EXAMPLE 7

CRACKING WITH PROTONIC ACID

Cracking was carried out in the like manner as in Example 6 by changing the kinds of catalysts. The results are shown in the following Table 6.

TABLE 6

| Experiment Number | Catalyst | Introduced Gas | Ratio of Cracking (%) | Content of Substituted Ethylene Component (wt. %) |
|---|---|---|---|---|
| 7-1 | Phosphoric acid | Nitrogen | 87 | 0.3 |
| 7-2 | Naphthalenesulfonic acid | Hydrogen | 76 | 0.5 |

COMPARATIVE EXAMPLE 5

Cracking of 1,1-di(dimethylphenyl)ethane was carried out in the like manner as in Example 6. The ratio of cracking was 83% and the content of substituted ethylene component in the unreacted 1,1-di(dimethylphenyl)ethane fraction was 12.3%.

REFERENCE EXAMPLE

PREPARATION OF 1,2-DI(4-ISOBUTYLPHENYL)ETHANE

REFERENCE EXAMPLE 1

SYNTHESIS OF DI(4-ISOBUTYLPHENYL)IODONIUM SALT

A mixture of 107 g of potassium periodate, 134 g of isobutylbenzene and 400 ml of acetic anhydride was fed into a three-neck flask having a cooling tube and the contents were stirred at 5 to 10° C. A mixture of 204 g of acetic anhydride and 196 g of concentrated sulfuric acid was added dropwise little by little to the above mixture over two hours. The temperature of reaction was maintained at 5 to 10° C. After the temperature of the reaction mixture was restored to room temperature, the stirring was continued for further 16 hours.

This reaction mixture was poured into ice water of 600 ml. By adding then a saturated aqueous solution of 100 g of potassium bromide, diisobutyl iodonium salt was crystallized out. Water was separated from this crystal by reduced pressure filtration and the crystal was further washed with water and subjected to reduced pressure filtration, again. This was dried in vacuum at 50° C. to obtain 167 g of di(4-isobutylphenyl)iodonium bromide (melting point: 180 to 182° C.).

REFERENCE EXAMPLE 2

REACTION OF ETHYLENE WITH DI(4-ISOBUTYLPHENYL)IODONIUM SALT

A mixture of 94.6 g of di(4-isobutylphenyl)iodonium bromide, 37 g of tri-n-butylamine, 2 g of palladium acetate and 500 ml of methanol was fed into 1 liter flask equipped with a reflux condenser and a stirrer. Then, with supplying 100 ml/min of ethylene gas, the contents were stirred at 50° C. for 16 hours.

After the reaction, methanol was evaporated off under reduced pressure. After 1 liter of water was added to this solution, extraction with toluene was carried out. The toluene layer was dried with magnesium sulfate and then filtered. After that, toluene was evaporated under reduced pressure. The remained liquid was subjected to recrystallization using methanol as a solvent to obtain 25 g of crystal having a melting point of 106 to 108° C.

The purity of this crystal was 98.0% and it was confirmed that the crystal was 4-diisobutylstilbene (=1,2-di(4-isobutylphenyl)ethylene) by IR analysis and NMR analysis.

Elemental Analysis: (as $C_{22}H_{28}$) C: 90.45% (calc'd 90.35%) H: 9.55% (calc'd 9.65%).

IR: (KBr method, $cm^{-1}$) 810, 850, 970, 1370, 1390, 1470, 1610, 1910, 2970, 3030.

NMR ($^1$H-NMR, δ) 0.9 Doublet ( 12H ) 1.8–2.0 Multiplet ( 2H ) 2.5 Doublet ( 4H ) 7.0 Singlet ( 2H ) 7.0–7.5 Multiplet ( 8H ).

REFERENCE EXAMPLE 3

HYDROGENATION OF 1,2-DI(4-ISOBUTYLPHENYL)ETHYLENE

To a 1 liter autoclave were fed 5 g of 1,2-di(4-isobutylphenyl)ethylene, 200 ml of diethyl ether and 0.5 g of Pd-carbon catalyst (5% Pd, made by Nippon Engelhard, Ltd.). The pressure was then raised to 10 kg/cm$^2$ by supplying pure hydrogen. Stirring was continued for 16 hours under the same pressure. After the reaction, unreacted hydrogen gas was exhausted to restore it to atmospheric pressure. The catalyst was then filtered off to obtain an ether solution. The ether was removed by evaporation and 4.8 g of crystal was obtained. The crystal was further subjected to recrystallization with methanol, thereby obtaining 4.3 g flaky crystal of 1,2-di(4-isobutylphenyl)ethane.

In the following, the results of analysis of this product are shown.

Melting Point: 29 to 31° C.

Elemental Analysis: (as $C_{22}H_{30}$) C: 89.71% (calc'd 89.73%) H: 10.29% (calc'd 10.27%)

IR: (KBr method, $cm^{-1}$) 795, 840, 1020, 1110, 1170, 1370, 1390, 1470, 1510, 1620, 1680, 1790, 1900, 2970, 3030.

NMR ($^1$H-NMR, δ) 0.8–1.0 Doublet ( 12H ) 1.8–2.0 Multiplet ( 2H ) 2.4–2.6 Doublet ( 4H ) 2.9 Singlet ( 4H ) 7.0–7.3 Multiplet ( 8H ).

EXAMPLE 8

CRACKING OF 1,2-DI(4-ISOBUTYLPHENYL)ETHANE

A silica-alumina catalyst (trademark: N-631-L, made by Nikki Chemical Corp.) of 15 to 25 mesh was prepared. It was fed as deep as 135 mm into a reaction tube of 12 mm in inner diameter made of stainless steel. This was heated to 500° C. by an electric furnace and cracking was carried out by continuously feeding 15 ml/hr of 1,2-di(4-isobutylphenyl)ethane and 150 ml/hr of water. After cooling the outlet of the reaction tube, the oily layer was separated from 6 hours to 54 hours after the start of reaction and it was subjected to gas chromatographic analysis. The results are shown in the following Table 7.

TABLE 7

| Results of Gas Chromatographic Analysis | |
|---|---|
| Fraction | Weight (%) |
| Lighter fraction | 0.6 |
| Isobutylbenzene fraction | 13.3 |
| 4-Isobutylethylbenzene fraction | 1.8 |
| 4-Isobutylstyrene fraction | 11.3 |
| Unreacted 1,2-di(4-isobutylphenyl)ethane fraction | 72.3 |
| Heavier fraction | 0.7 |

The product of cracking was subjected to precision fractional distillation to obtain a 4-isobutylstyrene fraction (recovery rate: 88%) in a distillation temperature range of 74 to 89° C. under a reduced pressure of 30 to 34 mmHg and a recovered fraction of unreacted 1,2-di(4-isobutylphenyl)ethane (recovery rate: 92%) in a distillation temperature range of 178 to 185° C. under a reduced pressure of 2 to 3 mmHg.

The bromine number of 1,2-(4-isobutylphenyl)ethane fraction, corresponding to the recovered unreacted fraction, was 0.20. According to mass spectrometry, the content of component of m/e=292 was 0.3% (m/e of 1,1-di(4-isobutylphenyl)ethane is 294).

COMPARATIVE EXAMPLE 6

CRACKING OF 1,1-DI(4-ISOBUTYLPHENYL)ETHANE

4-Isobutylbenzene and acetaldehyde were reacted in the presence of sulfuric acid catalyst. With regard to 1,1-di(4-isobutylphenyl)ethane (bromine number: 0.16) of 177 to 184° C. in distillation temperature at 2 to 3 mmHg was cracked in the like manner as in Example 8.

It was subjected to gaschromatographic analysis, the results of which are shown in the following Table 8.

TABLE 8

| Results of Gas Chromatographic Analysis | |
|---|---|
| Fraction | Weight (%) |
| Lighter fraction | 2.7 |
| Isobutylbenzene fraction | 24.6 |
| 4-Isobutylethylbenzene fraction | 2.3 |
| 4-Isobutylstyrene fraction | 24.8 |
| Unreacted 1,1-di(4-isobutylphenyl)ethane fraction | 44.3 |
| Heavier fraction | 1.3 |

The product of cracking was subjected to precision fractional distillation to obtain a 4-isobutylstyrene fraction (recovery rate: 73%) and a recovered fraction of unreacted 1,1-di(4-isobutylphenyl)ethane (recovery rate: 91%) in a distillation temperature range of 175 to 185° C. under a reduced pressure of 2 to 3 mmHg.

The bromine number of the recovered 1,1-di(4-isobutylphenyl)ethane fraction was 3.5. According to mass spectrometry, the content of component of m/e292 was 6.0% (m/e of 1,1-di(4-isobutylphenyl)ethane is 294).

EXAMPLE 9

RE-CRACKING OF RECOVERED FRACTION

The diarylethane fractions corresponding to the fractions of unreacted materials which were recovered in Example 8 and Comparative Example 6 were cracked intact in the like manner as in Example 8 to compare the changes in the ratios of cracking with the passage of time in the cracking reaction.

The results are shown in the following Table 9.

TABLE 9

| | Changes in Ratios of Cracking with the Passage of Time[*1] | | | | |
|---|---|---|---|---|---|
| Fraction | 12 hr | 24 hr | 48 hr | 72 hr | Content[*2] |
| Example 8 | 0.88 | 0.67 | 0.54 | 0.53 | 0.3 |
| Comp. Ex. 6 | 0.83 | 0.51 | 0.39 | 0.31 | 8.2 |

Notes [*1] and [*2] are the same as those in Table 3.

As will be understood from the above results, the change in the ratio of catalytic cracking with the passage of time in the recovered fraction of Example 8 is smaller as compared with that of Comparative Example 6.

EXAMPLE 10

Using catalysts shown in the following Table 10, 1,2-di(4-isobutylphenyl)ethane was cracked in the like manner as in Example 8. The results of them are shown also in Table 10.

TABLE 10

| Experiment Number | Catalyst | Ratio of Cracking (%) | Content of Substituted Ethylene Component (wt. %) |
|---|---|---|---|
| | Clay-type solid catalyst | | |
| 10-1 | Kaolin clay | 32 | 0.3 |
| 10-2 | Attapulgus clay (made by Nippon Engelhard, Ltd) | 26 | 0.2 |
| | Synthetic silica-alumina solid catalyst | | |
| 10-3 | FCC-HA (trademark, made by Catalyst & Chem. Ind. Co.) | 31 | 0.2 |
| | Zeolite-type solid catalyst | | |
| 10-4 | MR-Z (trademark, made by Catalyst & Chem. Ind. Co.) | 33 | 0.3 |

What is claimed is:

1. A method for producing 4-isobutylstyrene which is characterized in that 1,2-di(4-isobutylphenyl)ethane is brought into contact with an acid catalyst at 200° C. to 650° C. in the presence of an inert gas at a dilution ratio of at least 50 moles of inert gas per mole of 1,2-di(4-isobutylphenyl)ethane to crack it into 4-isobutylstyrene and isobutylbenzene 2. The method for producing 4-isobutylstyrene according to claim 1, wherein said acid catalyst is a protonic acid catalyst, a solid acid catalyst, or a solid catalyst carrying a protonic acid.

3. The method for producing 4-isobutylstyrene according to claim 2, wherein said solid acid is acidic clay, acidic synthetic silica-alumina or acidic zeolite.

4. The method for producing 4-isobutylstyrene according to claim 2, wherein said protonic acid is an inorganic protonic acid, or an organic protonic acid.

5. The method for producing 4-isobutylstyrene according to claim 4, wherein said inorganic acid is phosphoric acid.

6. The method for producing 4-isobutylstyrene according to claim 4, wherein said organic acid is naphthalenesufonic acid.

7. The method for producing 4-isobutylstyrene according to claim 4, wherein said inorganic protonic acid is a heteropolyacid.

8. The method for producing 4-isobutylstyrene according to claim 7, wherein said heteropolyacid is silicotungstic acid.

9. The method for producing 4-isobutylstyrene according to claim 1, wherein unreacted 1,2-di(4-isobutylphenyl)ethane is recovered from the reaction mixture, and is thereafter brought into contact with said acid catalyst at 200° C. to 650° C. in the presence of an inert gas to crack it into 4-isobutylstyrene and isobutylbenzene.

10. The method for producing 4-isobutylstyrene according to claim 9, wherein said catalyst is a protonic acid catalyst, a solid acid catalyst or a solid catalyst carrying a protonic acid.

11. The method for producing 4-isobutylstyrene according to claim 10, wherein said solid acid is acidic clay, acidic synthetic silica-alumina or acidic zeolite.

12. The method for producing 4-isobutylstyrene according to claim 10, wherein said protonic acid is an inorganic protonic acid or an organic protonic acid.

13. The method for producing 4-isobutylstyrene according to claim 12, wherein said inorganic acid is phosphoric acid.

14. The method for producing 4-isobutylstyrene according to claim 12, wherein said organic acid is naphthalenesulfonic acid.

15. The method for producing 4-isobutylstyrene according to claim 12 wherein said inorganic protonic acid is a heteropolyacid.

16. The method for producing 4-isobutylstyrene according to claim 15, wherein said heteropolyacid is silicotungstic acid.

* * * * *